US010831022B2

(12) United States Patent
Kobashigawa et al.

(10) Patent No.: US 10,831,022 B2
(45) Date of Patent: Nov. 10, 2020

(54) INFORMATION DISPLAY DEVICE

(71) Applicant: Ricoh Company, Ltd., Tokyo (JP)

(72) Inventors: Shohta Kobashigawa, Tokyo (JP); Yumiko Kishi, Kanagawa (JP); Hiroki Hiraguchi, Tokyo (JP); Naoki Sakai, Kanagawa (JP)

(73) Assignee: RICOH COMPANY, LTD., Tokyo (JP)

( * ) Notice: Subject to any disclaimer, the term of this patent is extended or adjusted under 35 U.S.C. 154(b) by 151 days.

(21) Appl. No.: 16/099,477

(22) PCT Filed: May 8, 2017

(86) PCT No.: PCT/JP2017/017404
§ 371 (c)(1),
(2) Date: Nov. 7, 2018

(87) PCT Pub. No.: WO2017/203964
PCT Pub. Date: Nov. 30, 2017

(65) Prior Publication Data
US 2019/0162958 A1 May 30, 2019

(30) Foreign Application Priority Data
May 23, 2016 (JP) .................................. 2016-102552

(51) Int. Cl.
*G02B 27/01* (2006.01)
*A61B 3/00* (2006.01)
*A61B 3/06* (2006.01)
(52) U.S. Cl.
CPC ........ *G02B 27/0101* (2013.01); *A61B 3/0033* (2013.01); *A61B 3/066* (2013.01);
(Continued)
(58) Field of Classification Search
CPC .............................................. G02B 27/0101
(Continued)

(56) References Cited

U.S. PATENT DOCUMENTS 5,900,336 A    5/1999   Kabata et al.
6,272,071 B1   8/2001   Takai et al.
(Continued)

FOREIGN PATENT DOCUMENTS

DE   10 2013 019 550 B3   1/2015
EP        2 905 647 A1    8/2015
(Continued)

OTHER PUBLICATIONS

Office Action dated Feb. 12, 2020, issued in corresponding Japanese Patent Application No. JP2016-102552, 3 pages.
(Continued)

*Primary Examiner* — James C. Jones
(74) *Attorney, Agent, or Firm* — Xsensus LLP

(57) ABSTRACT (Object) To provide an information display device, with a simple configuration, that is capable of reducing stress in perceiving information. (Means of Achieving the Object) The disclosed information display device irradiates a transparent-reflective member with light for forming an image, in order to display a virtual image of the image on the transparent-reflective member. The information display device includes: a plurality of light sources having different peak emission wavelengths, respectively, which are provided for generating the light for forming the image; a vision-related information input unit configured to receive an input of information relating to vision of a viewer viewing the virtual image; and a luminance adjusting unit configured to adjust luminance of each of the plurality of light sources, independently, based on the information input into the vision-related information input unit.

11 Claims, 7 Drawing Sheets

(52) U.S. Cl.
CPC .............. *G02B 2027/0112* (2013.01); *G02B 2027/0118* (2013.01); *G02B 2027/0141* (2013.01); *G02B 2027/0181* (2013.01)

(58) Field of Classification Search
USPC ................................ 351/237; 359/630, 631
See application file for complete search history.

(56) References Cited

U.S. PATENT DOCUMENTS

| | | |
|---|---|---|
| 8,024,300 B2 | 9/2011 | Hiraguchi |
| 8,085,431 B2 | 12/2011 | Kishi |
| 8,289,543 B2 | 10/2012 | Murata et al. |
| 8,547,587 B2 | 10/2013 | Miyazaki et al. |
| 8,570,582 B2 | 10/2013 | Torii et al. |
| 8,599,442 B2 | 12/2013 | Yukumoto et al. |
| 8,918,041 B2 | 12/2014 | Kobashigawa |
| 8,983,348 B2 | 3/2015 | Kobashigawa et al. |
| 9,100,611 B2 | 8/2015 | Kishi et al. |
| 9,164,447 B2 | 10/2015 | Kobashigawa et al. |
| 9,519,248 B2 | 12/2016 | Matsusaka et al. |
| 9,612,555 B2 | 4/2017 | Yoshinaga et al. |
| 9,612,556 B2 | 4/2017 | Ogino et al. |
| 9,618,886 B2 | 4/2017 | Seto et al. |
| 9,639,042 B2 | 5/2017 | Ishii et al. |
| 9,651,905 B2 | 5/2017 | Fujimoto et al. |
| 9,678,460 B2 | 6/2017 | Hase et al. |
| 9,778,606 B2 | 10/2017 | Seki et al. |
| 9,829,840 B2 | 11/2017 | Seto et al. |
| 9,851,663 B2 | 12/2017 | Kobashigawa et al. |
| 9,874,839 B2 | 1/2018 | Sawada et al. |
| 9,905,018 B2 | 2/2018 | Sakai |
| 2009/0232351 A1 | 9/2009 | Kagitani et al. |
| 2012/0235805 A1* | 9/2012 | Nogami ................ G06T 7/215 340/441 |
| 2015/0260984 A1 | 9/2015 | Yamakawa et al. |
| 2015/0302773 A1 | 10/2015 | Stone et al. |
| 2015/0316765 A1* | 11/2015 | Kim ...................... H04N 5/247 345/7 |
| 2016/0173867 A1 | 6/2016 | Ichihashi et al. |
| 2016/0246228 A1 | 8/2016 | Fujimoto et al. |
| 2016/0277610 A1 | 9/2016 | Kishi et al. |
| 2017/0230628 A1 | 8/2017 | Ichikawa et al. |

FOREIGN PATENT DOCUMENTS

| | | |
|---|---|---|
| JP | 09-097333 A | 4/1997 |
| JP | 11-016091 | 1/1999 |
| JP | 11-285022 A | 10/1999 |
| JP | 2005-75081 A | 3/2005 |
| JP | 2006-013905 A | 1/2006 |
| JP | 2009-301323 A | 12/2009 |
| JP | 2010-58742 A | 3/2010 |
| JP | 2012-121527 A | 6/2012 |
| JP | 2014-074818 A | 4/2014 |
| JP | 2015-134521 A | 7/2015 |
| JP | WO 2015/146042 A1 | 10/2015 |
| JP | 2016-25394 A | 2/2016 |
| JP | 2017-142491 A | 8/2017 |
| KR | 2000-0074925 | 12/2000 |
| KR | 10-0664957 | 1/2007 |

OTHER PUBLICATIONS

International Search Report and Written Opinion dated Aug. 21, 2017 in PCT/JP2017/017404 filed on May 8, 2017.

Okajima et al., "Simulation of Light Efficiency for Aged People and Data-Analysis of an Optimal Illuminance with Aging Models of the Human Lens," The Illuminating Engineering Institute of Japan, vol. 82, No. 8A, 1998, pp. 564-572 (with English abstract and partial translation).

Office Action dated Jun. 23, 2020 in Japanese Patent Application No. 2016-102552, 2 pages.

* cited by examiner

[Fig. 1]
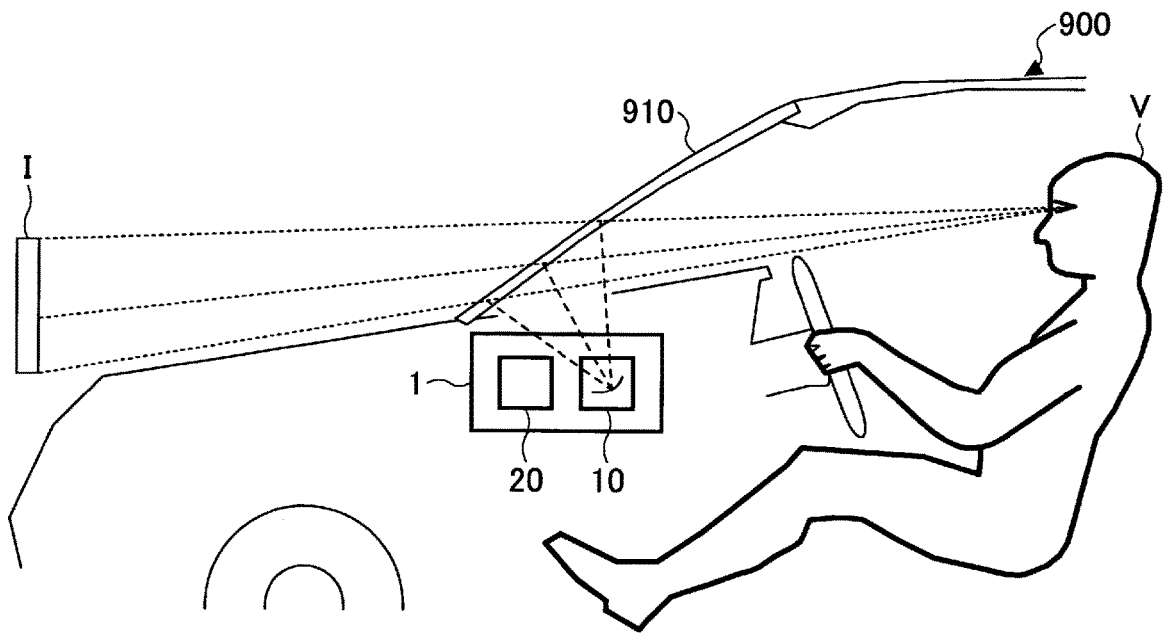
[Fig. 2]
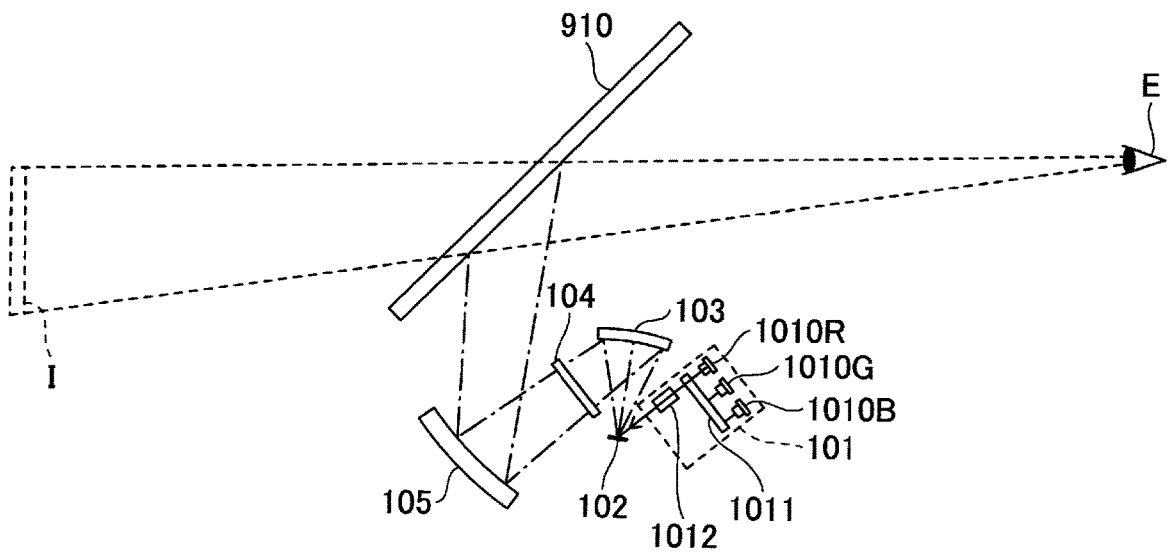

[Fig. 3]
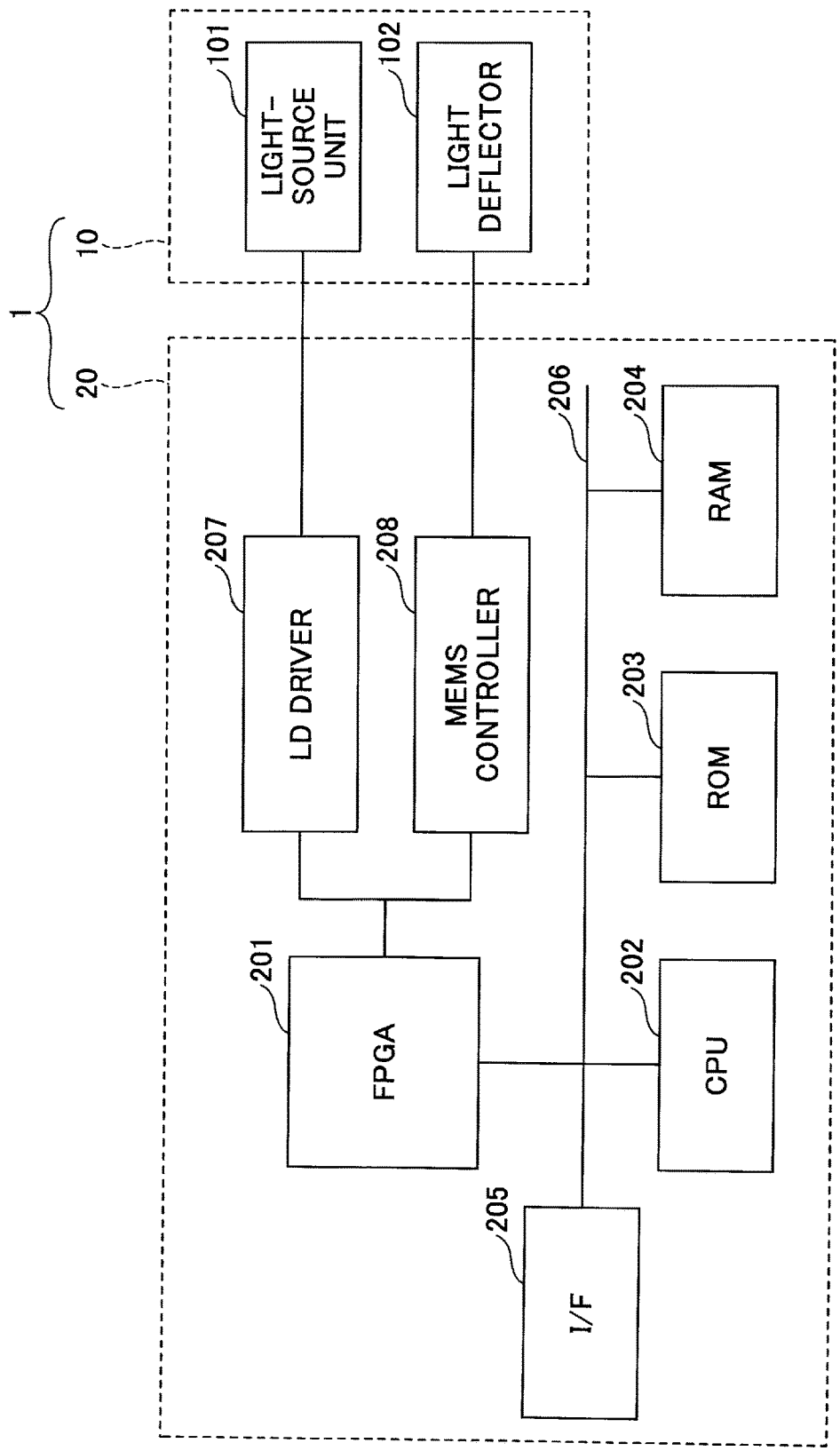

[Fig. 4]
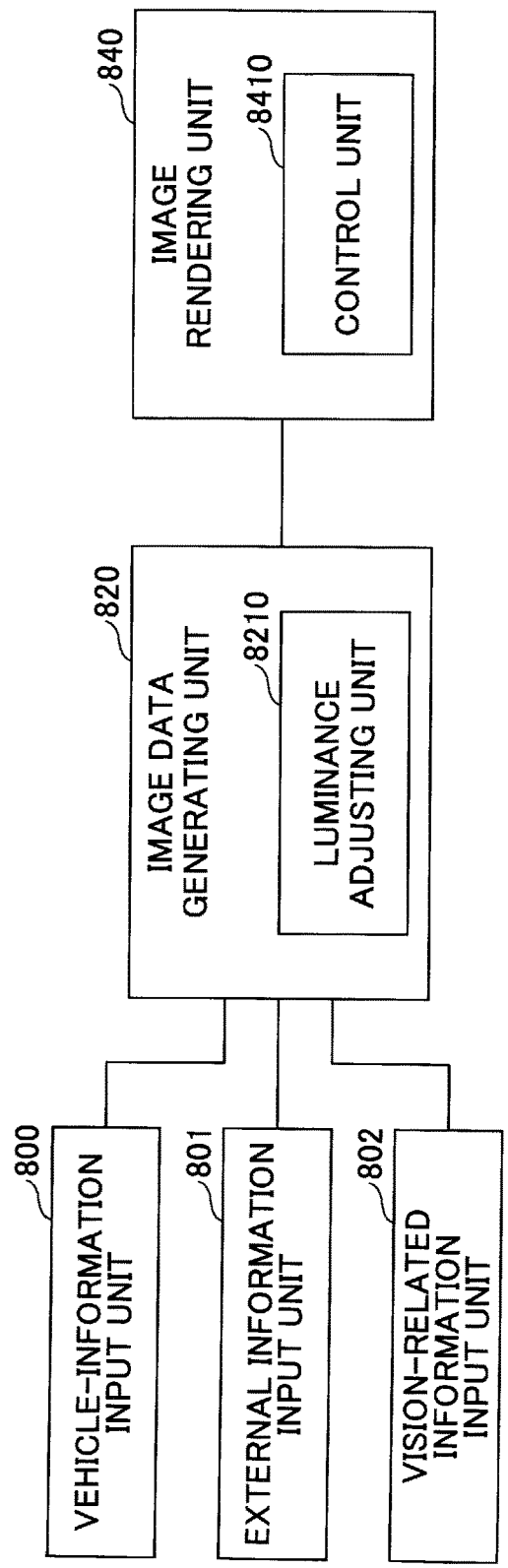

[Fig. 5]
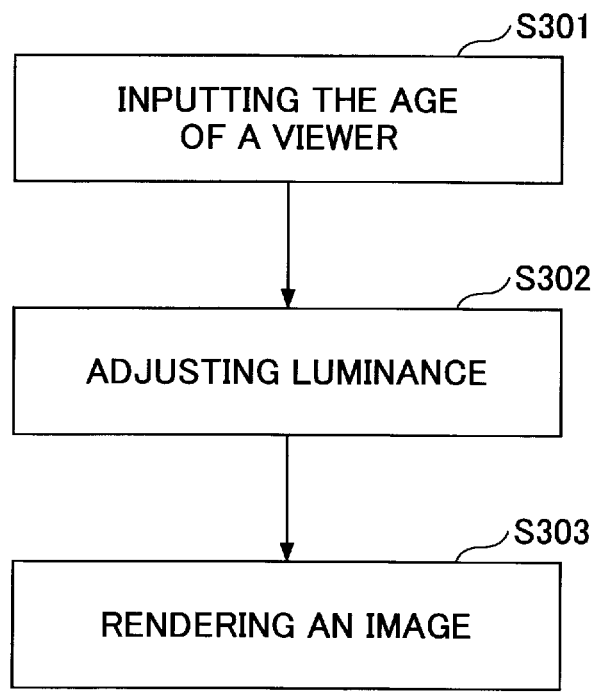
[Fig. 6]
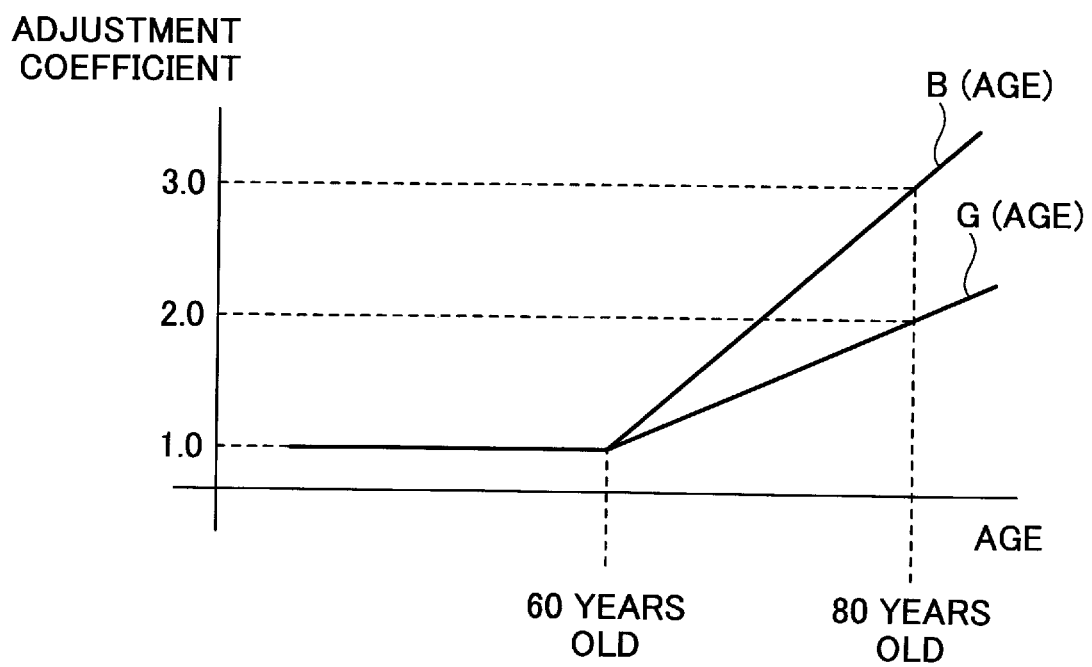

[Fig. 7]
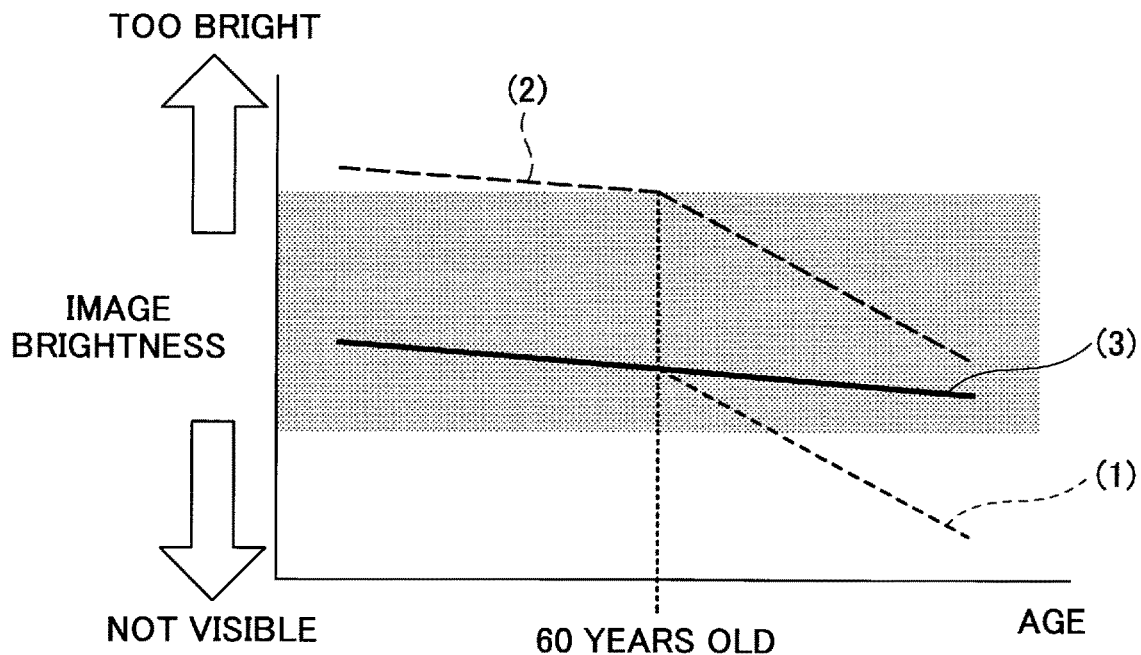
[Fig. 8]
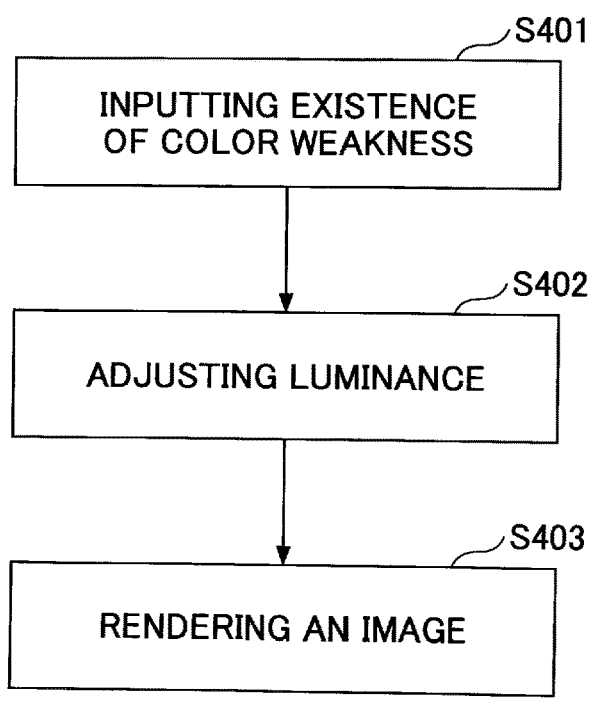

[Fig. 9]
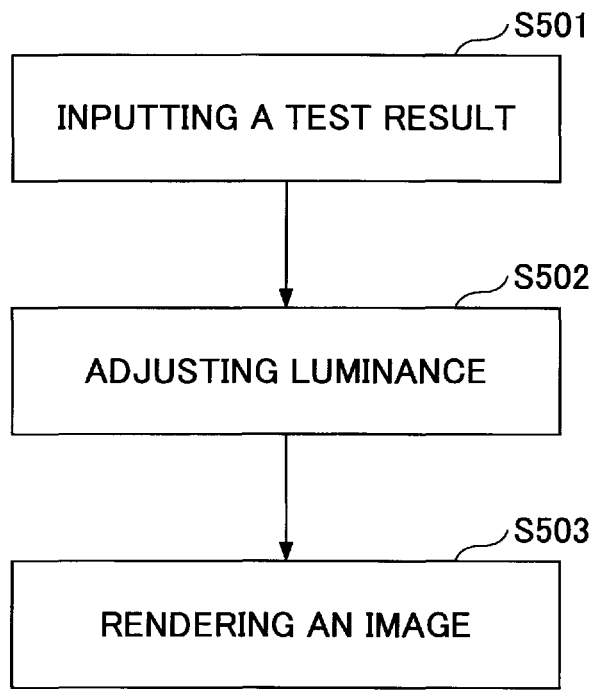
[Fig. 10A]
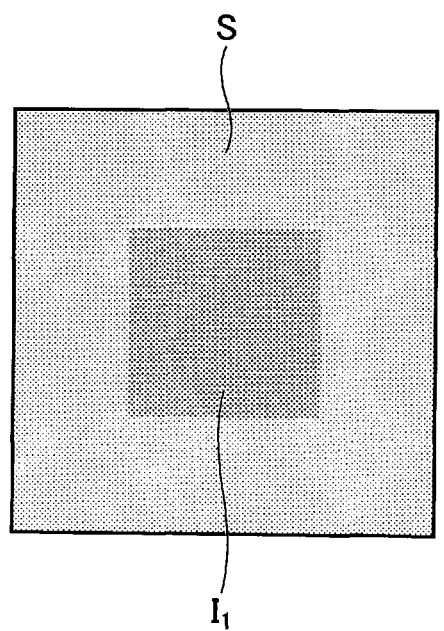

[Fig. 10B]
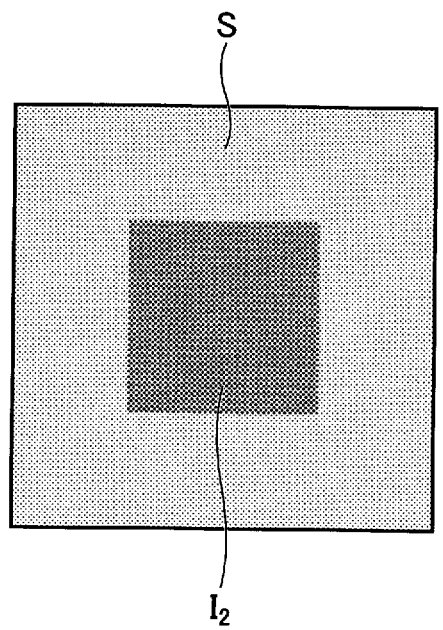
[Fig. 10C]
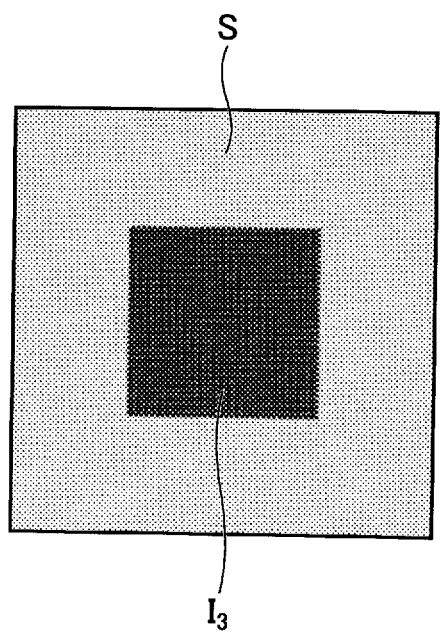

INFORMATION DISPLAY DEVICE

TECHNICAL FIELD

The present invention relates to information display devices.

BACKGROUND ART

Progress has been made in development of technologies relating to head-up displays (hereinafter referred to as HuDs) to be mounted on a vehicle as an application for a driver to perceive alarms and information with less movement of eyes. In particular, with progress of in-vehicle sensing technologies as typified by the term "advanced driving assistance system (ADAS)", it has been possible for a vehicle to collect various types of information about driving environments and passengers of the vehicle, and attention has been paid to HuDs as an "output of ADAS" for providing such information to a driver.

There is a demand from the market that an HuD, which is an information display device, is compact and of low stress in perceiving information. Especially, being of low stress in perceiving information is important. That is to say, as images generated by an HuD are displayed near a driver's eyesight all the time, image expression that is not stressful to the driver and is friendly to individual differences between drivers is demanded. Accordingly, technologies attending to such a demand have been disclosed.

For example, there exists an information display device including: an information display determination unit configured to acquire information regarding condition of a vehicle and to determine information that should be displayed at an HuD, on the basis of the acquired information; an image processing unit configured to acquire an image formed by imaging an area in front of the vehicle; a gaze direction detection unit configured to detect a gaze direction of the driver; a virtual view building unit configured to build a virtual view image being an image corresponding to the field of vision of the driver, on the basis of the image of the area in front of the vehicle and the gaze direction of the driver; and a display processing unit configured to determine layout of the information to be displayed at the HuD, on the basis of the virtual view image and the condition of the vehicle (see, for example, PTL 1).

CITATION LIST

Patent Literature

[PTL 1] Japanese Unexamined Patent Application Publication No. 2015-134521

SUMMARY OF INVENTION

Technical Problem

However, although the above-proposed information display device detects an image of an area in front of a vehicle by means of a sensor, etc., and changes layouts of information to be displayed, based on a detection result, the information display device requires a very complicated mechanism for detection and control, which involves a problem of high cost.

The present invention is provided to attend to the above problem and aims to provide an information display device, with a simple configuration, that is capable of reducing stress in perceiving information.

Solution to Problem

The disclosed information display device irradiates a transparent-reflective member with light for forming an image, in order to display a virtual image of the image on the transparent-reflective member. The information display device includes: a plurality of light sources having different peak emission wavelengths, respectively, which are provided for generating the light for forming the image; a vision-related information input unit configured to receive an input of information relating to vision of a viewer viewing the virtual image; and a luminance adjusting unit configured to adjust luminance of each of the plurality of light sources, independently, based on the information input into the vision-related information input unit.

Advantageous Effects of Invention

According to the disclosed technique, an information display device, with a simple configuration, that is capable of reducing stress in perceiving information can be provided.

BRIEF DESCRIPTION OF DRAWINGS

FIG. 1 is a schematic diagram illustrating an example of an information display device according to a first embodiment;

FIG. 2 is a drawing illustrating an example of a configuration of an optical unit provided in the information display device according to the first embodiment;

FIG. 3 is a block diagram illustrating an example of a hardware configuration of the information display apparatus according to the first embodiment;

FIG. 4 is a block diagram illustrating an example of functions of the information display device according to the first embodiment;

FIG. 5 is a flowchart illustrating an example of luminance adjustment according to the first embodiment;

FIG. 6 is a drawing illustrating relations between ages and luminance adjustment coefficients, according to the first embodiment;

FIG. 7 is a drawing illustrating an example of a result of a subjectively-viewed evaluation whether luminance is high enough for a viewer to clearly perceive an image, according to the first embodiment;

FIG. 8 is a flowchart illustrating an example of luminance adjustment according to a second embodiment;

FIG. 9 is a flowchart illustrating an example of luminance adjustment according to a third embodiment;

FIG. 10A is a drawing illustrating an example of a checking method of visual faculties of a viewer, according to the third embodiment;

FIG. 10B is a drawing illustrating an example of the checking method of visual faculties of a viewer, according to the third embodiment; and FIG. 10C is a drawing illustrating an example of the checking method of visual faculties of a viewer, according to the third embodiment.

DESCRIPTION OF EMBODIMENTS

The following description explains embodiments of the present invention, with reference to drawings. In the draw-

First Embodiment (Overview of the Information Display Apparatus)

FIG. 1 is a schematic diagram illustrating an example of an information display device according to the first embodiment. Referring to FIG. 1, an information display device 1 is mounted on a subject-vehicle 900. The information display device 1 is what is called an HuD that has a function to project a predetermined image on a front windshield 910, which is in front of a viewer V, so as to display a virtual image I superimposed in the field of view of the viewer V. Note that the viewer V is a driver, who is a passenger of the subject-vehicle 900. The front windshield 910 functions as a transparent-reflective member, which passes a part of incident light through and reflects at least a part of the remainder.

The information display device 1 can be arranged to be at a selectable position, in conformity with interior design of the subject-vehicle 900. For example, the information display device 1 may be arranged on the dashboard of the subject-vehicle 900. The information display device 1 may be embedded in the dashboard of the subject-vehicle 900. Main constituent elements of the information display device 1 include an optical unit 10 and an electronics unit 20.

Note that, although the information display device 1 is mounted on the subject-vehicle 900 in the example of the first embodiment, the information display device 1 is not limited to be as such. For example, the information display device 1 may be mounted on a movable object such as a car, a plane, a ship, or an industrial robot, in order to enable navigation information, which is needed for controlling such a movable object, to be seen on a front windshield of the movable object. Note that the navigation information is, for example, speed and a moving direction of a movable object, distance to a destination, a name of a current place, existence of an object (i.e. an actual object) in front of a moving object as well as a position of the object, a speed limit sign, information of traffic backup, etc.

Projection methods of the information display device 1 include a panel method and laser-scan method. In a panel method, an intermediate image is formed by means of an imaging device such as a liquid crystal panel, a digital mirror device (DMD) panel, or a vacuum fluorescent display (VFD). Contrarily, in a laser-scan method, an intermediate image is formed by means of a two-dimensional scanning device, which performs scanning with a laser beam emitted by a laser light source.

A laser-scan method, in which emission or non-emission of light is assigned for each pixel, is generally preferred for the reason of an ability to form high-contrast images, unlike a panel method, in which images are formed by partially shielding light emission of the entire screen. Although a laser-scan method is used as the projection method of the information display device 1 in the example of the first embodiment, the projection method is not limited to as such.

FIG. 2 is a drawing illustrating an example of a configuration of an optical unit provided in the information display device according to the first embodiment. Referring to FIG. 2, roughly, the optical unit 10 includes a light source unit 101, a light deflector 102, a mirror 103, a screen 104, and a concave mirror 105.

When the front windshield 910 is irradiated from the optical unit 10 with light (i.e. image light) to form an image, a virtual image I of an image can be seen from a viewing point E (i.e. the midpoint between the right and left eyes) of the viewer V. In other words, the viewer V can see, via the front windshield 910, a virtual image I of an image (i.e. intermediate image) formed (or rendered) on the screen 104 of the optical unit 10. The intermediate image is an information-providing image for providing information to the viewer V.

The following description explains an example of a configuration of the optical unit 10 in detail. The light source unit 101 includes lasers 1010R, 1010G, and 1010B, which are light sources, a light-path integrating unit 1011, and an optical system 1012. The lasers 1010R, 1010G, and 1010B have different peak emission wavelengths, respectively.

The laser 1010R is a light source of red (R); for example, the laser 1010R may be a red semiconductor laser, which emits a laser beam in a peak emission wavelength of 600 nm or more and less than 680 nm. The laser 1010G is a light source of green (G); for example, the laser 1010G may be a green semiconductor laser, which emits a laser beam in a peak emission wavelength of 495 nm or more and less than 570 nm. The laser 1010B is a light source of blue (B); for example, the laser 1010B may be a blue semiconductor laser, which emits a laser beam in a peak emission wavelength of 450 nm or more and less than 495 nm.

Laser beams emitted from the lasers 1010R, 1010G, and 1010B pass through coupling lenses, apertures, etc., which are provided as needed, and then are integrated at the light-path integrating unit 1011, which is a dichroic mirror, etc. The integrated laser beam is guided by the optical system 1012 to a reflecting surface of the light deflector 102. The optical system 1012 is configured, for example, by a combination of multiple lenses.

A laser beam guided to the reflecting surface of the light deflector 102 is two-dimensionally deflected by the light deflector 102. The light deflector 102 may be, for example, a single micro-mirror that swings with respect to two axes perpendicular to each other, two micro-mirrors that swing or rotate with respect to different axes, respectively, etc. The light deflector 102 may be, for example, micro electro mechanical systems (MEMS), which are fabricated in a semiconductor fabricating process, etc. The light deflector 102 may be driven, for example, by an actuator utilizing deformation force of a piezoelectric element as driving force. The light deflector 102 may be a galvanometer mirror, a polygon mirror, etc.

A laser beam that is two-dimensionally deflected by the light deflector 102 enters the mirror 103 and is reflected by the mirror 103, and then renders a two-dimensional image (i.e. an intermediate image) on a surface (i.e. the scanned surface) of the screen 104. The mirror 103 may be, for example, a concave mirror, a convex mirror or a plane mirror. The screen 104 is preferred to be a micro-lens array or a micro-mirror array, which has a function to diverge a laser beam at a desired divergence angle, although the screen 104 may be a diffuser plate that diffuses a laser beam, a transparent plate or a reflective plate with a flat surface, etc., as well.

A laser beam projected from the screen 104 is reflected by the concave mirror 105, and then is incident on the front windshield 910. A part of light flux that is incident on the front windshield 910 passes through the front windshield 910 and at least a part of the remainder is reflected to the viewing point E. As a result, the viewer V can see a virtual image I, which is a magnified image of an intermediate image, via the front windshield 910. That is to say, a magnified virtual image I is displayed on the front windshield 910 so as to be seen by the viewer V.

Commonly, the front windshield 910 is not flat but slightly curved. Thus, an image location of a virtual image I is determined in accordance with the concave mirror 105 and the curved surface of the front windshield 910.

Additionally, it is preferred that at least one of the mirror 103 and the concave mirror 105 is designed/arranged so as to correct optical distortion caused by the shape of the front windshield 910, due to which a horizontal line of an intermediate image becomes convex or concave.

Additionally, a combiner may be provided, as a transparent-reflective member, inside the front windshield 910. Similarly to a case of irradiating the front windshield 910 with light from the concave mirror 105, a virtual image I may be displayed by irradiating the combiner with light from the concave mirror 105.

FIG. 3 is a block diagram illustrating an example of a hardware configuration of the information display apparatus according to the first embodiment. Referring to FIG. 3, the electronics unit 20 includes a field-programmable gate array (FPGA) 201, a central processing unit (CPU) 202, a read-only memory (ROM) 203, a random access memory (RAM) 204, an interface (I/F) 205, a bus-line 206, a laser diode (LD) driver 207, and a micro-electro-mechanical systems (MEMS) controller 208. The FPGA 201, the CPU 202, the ROM 203, the RAM 204, and the I/F 205 are interconnected via the bus-line 206.

The FPGA 201 drives the lasers 1010R, 1010G, and 1010B of the light source unit 101 provided in the optical unit 10, by means of the LD driver 207. Furthermore, the FPGA 201 drives the light deflector 102 provided in the optical unit 10, by means of the MEMS controller 208.

The CPU 202 controls each function of the information display device 1. The ROM 203 stores programs executed by the CPU 202 to control each function of the information display device 1. The RAM 204 is used as a work area of the CPU 202.

The I/F 205 is an interface to connect to another device, etc. For example, the I/F 205 is connected to a controller area network (CAN) of a car, an external network, or an input device such as a touchscreen or a keyboard.

FIG. 4 is a block diagram illustrating an example of functions of the information display device according to the first embodiment. Referring to FIG. 4, the information display device 1 includes a vehicle-information input unit 800, an external information input unit 801, a vision-related information input unit 802, an image data generating unit 820, and an image rendering unit 840. In order to actualize functions of each block as illustrated in FIG. 4, the CPU 202 illustrated in FIG. 3 executes predetermined programs and, if needed, cooperates with other hardware resources, although a part or the entirety of functions of each part as illustrated in FIG. 4 may be actualized by hardware such as an FPGA.

To the vehicle-information input unit 800, information relating to a vehicle (e.g. information such as speed and travel distance) is input from a CAN, etc. To the external information input unit 801, information relating to the outside of a vehicle (e.g. navigation information from global positioning system (GPS)) is input from an external network. To the vision-related information input unit 802, information relating to viewer's vision of a virtual image is input from an input device such as a touchscreen or a keyboard. Information input to the vehicle-information input unit 800, the external information input unit 801, and the vision-related information input unit 802 is transmitted to the image data generating unit 820.

The image data generating unit 820 generates image data representing an image to be rendered, based on information input through at least one of the vehicle-information input unit 800, the external information input unit 801, and the vision-related information input unit 802. Generated image data is transmitted to the image rendering unit 840.

The image data generating unit 820 includes a luminance adjusting unit 8210. At the time of generating image data, in a case where information has not been input through the vision-related information input unit 802, the luminance adjusting unit 8210 transmits a default setting value of luminance (i.e. pre-adjusted luminance) of the information display device 1 to the image rendering unit 840 as a part of the image data. At the time of generating image data, in a case where information has been input through the vision-related information input unit 802, the luminance adjusting unit 8210 adjusts luminance of each light source, independently, based on the information obtained from the vision-related information input unit 802, and then transmits adjusted luminance to the image rendering unit 840 as a part of the image data.

The image rendering unit 840 includes a control unit 8410, which controls the optical unit 10 in accordance with image data, so as to irradiate the front windshield 910 with light. As a result, a virtual image I can be seen from the viewing point E of the viewer V. As the image data includes luminance information received from the luminance adjusting unit 8210, the viewer V can see a virtual image I, which is based on the luminance information received from the luminance adjusting unit 8210.

(Luminance Adjustment Based on Information Obtained from the Vision-Related Information Input Unit 802)

The following description explains a case where an "age of a viewer" is input to the vision-related information input unit 802 as information relating to viewer's vision of a virtual image. Note that an age of a viewer is information relating to viewer's vision of a virtual image because visibility of each color of RGB changes, depending on age of viewers.

FIG. 5 is a flowchart illustrating an example of luminance adjustment according to the first embodiment. First, at Step S301, the age of a viewer of a virtual image is input through an input device such as a touchscreen or a keyboard, which is configured to be able to input information to the vision-related information input unit 802.

Information about the age of a viewer of a virtual image that is input to the vision-related information input unit 802 is sent to the image data generating unit 820. Note that the age of a viewer of a virtual image may be input through the input device by the viewer him/herself and may be input through the input device by a fellow passenger on a vehicle, etc., instead of the viewer.

Then, at Step S302, the luminance adjusting unit 8210 of the image data generating unit 820 performs luminance adjustment, based on the age of a viewer that is received from the vision-related information input unit 802. For example, in a case where default setting values of the lasers 1010R, 1010G, and 1010B provided in the information display device 1 are luminance IR1, IG1, and IB1, respectively, the luminance adjusting unit 8210 adjusts luminance IR1, IG1, and IB1 into luminance IR2, IG2, and IB2, respectively, based on the age of a viewer that is received from the vision-related information input unit 802.

For example, luminance IG2 and IB2 may be calculated through multiplication of adjustment coefficients G(AGE)

and B(AGE) to the default setting values, i.e., luminance IG1 and IB1, respectively, in accordance with the age of a viewer that is received from the vision-related information input unit 802. That is to say; IG2=G(AGE)×IG1; IB2=B(AGE)×IB1.

Note that luminance adjustment is not performed on luminance IR1 (i.e. adjustment coefficient is set to 1), such that IR2=IR1, because visual faculties to see red images do not significantly change by the age of a viewer, which means that even an aged person can see red images without adjustment.

For example, as illustrated in FIG. 6, adjustment coefficients G(AGE) and B(AGE) may be changed, depending on age (AGE). In the example of FIG. 6, adjustment coefficients for viewers at the age of 60 or less are both 1.0, which means that luminance of default setting values are not changed. Contrarily, as for viewers over the age of 60, luminance of light sources of blue and green light, among multiple light sources, are adjusted to be higher, compared to default setting values, proportionally with age of a viewer.

Specifically, adjustment coefficients are linearly increased with age of a viewer. Adjustment coefficients G(AGE) and B(AGE) for a viewer at the age of 80 are increased up to 2.0 and 3.0, respectively. Note that adjustment coefficients G(AGE) and B(AGE) are not limited to the example of FIG. 6; adjustment coefficients G(AGE) and B(AGE) may be determined through perception experiments, etc., conducted for viewers in various ages.

For example, in order to adjust luminance, data (i.e. relations between luminance IR1, IG1, and IB1 and luminance IR2, IG2, and IB2, respectively, depending on age) as illustrated in FIG. 6 may be stored in the ROM 203 in a table format or as coefficient data, so that the luminance adjusting unit 8210 can retrieve, from the ROM 203, an adjustment coefficient of luminance corresponding to an age. An adjusted value of luminance is sent to the image rendering unit 840 as a part of image data.

Then, at Step S303, the control unit 8410 of the image rendering unit 840 controls the optical unit 10, based on image data, so as to irradiate the front windshield 910 with light. Here, in a case where the age of a viewer is under 60, current values of the lasers 1010R, 1010G, and 1010B are independently controlled to be: IR2=IR1; IG2=IG1; and IB2=IB1, respectively; so that a virtual image in unadjusted luminance is displayed.

Contrarily, in a case where the age of a viewer is 60 or more, values of current for the lasers 1010R, 1010G, and 1010B are independently controlled to be: IR2=IR1; IG2=G(AGE)×IG1; and IB2=B(AGE)×IB1, respectively; so that a virtual image in desired luminance is displayed.

Note that, although the above description explains a case where 60 is a criterial age, there is no specific limitation of age. For example, in FIG. 6, a threshold value for changing adjustment coefficients need not be 60. Furthermore, in the example of FIG. 6, although adjustment coefficients are linearly increased proportionally with age of a viewer, adjustment coefficients are not limited to as such; adjustment coefficients may be increased non-linearly such as in a quadratic curve or may be increased according to a chart with stepwise increase, on which adjustment coefficients are stable in a range of ages and are changed to be in another range of ages.

Note that visual faculties of aged people to see colors of shorter wavelengths tend to be worse, which means that visibility of aged people is considered to be enhanced by increasing the adjustment coefficient B(AGE) proportionally with age of a viewer; and therefore, in an example of FIG. 6, adjustment coefficient B(AGE) is greater than adjustment coefficient G(AGE) for a viewer at the age of 60 or more. If needed, values of adjustment coefficients B(AGE) and G(AGE) may be the same. Further, multiplication of an adjustment coefficient may only apply to adjustment coefficient B(AGE), such that adjustment by use of adjustment coefficient G(AGE) is not performed, similarly to adjustment by use of adjustment coefficient R(AGE) being not performed.

Note that, according to a spectral transmittance ratio model of lenses of human eyes in different ages in "Simulation of Light Efficiency for Aged People and Data-Analysis of an Optimal Illuminance with Aging Models of the Human Lens" (Journal of the Illuminating Engineering Institute of Japan, Vol. 82, No. 8A, 1998), with respect to a light source of a peak emission wavelength under 520 nm, a spectral transmittance ratio of lenses of human eyes of aged people (i.e. people at an age of 60 or more and 80 or less) is 30% to 50% lower than that of young people (i.e. people at the age of 22).

Based on the above explanation, it is considered to be effective that, in a case where a viewer is an aged person, luminance of a light source of a peak emission wavelength under 520 nm, among multiple light sources, is adjusted to be higher, compared to a default setting value, proportionally with age of a viewer. In other words, it is effective that multiplication of an adjustment coefficient only applies to adjustment coefficient B(AGE), or to coefficients B(AGE) and G(AGE).

Specifically, in a case of using a light source of a peak emission wavelength under 520 nm, it is preferred that setting values of luminance intended for an aged person (i.e. person at the age of 60 or more and 80 or less) is 1.4 to 2.0 times higher than default setting values, to compensate for the light source of a peak emission wavelength under 520 nm. For example, in a case where a default setting value of luminance is 5000 cd/m$^2$, a setting value of luminance intended for an aged person (i.e. person at the age of 60 or more and 80 or less) is preferred to be 7000 to 10000 cd/m$^2$.

As described above, in the first embodiment, the information display device 1 adjusts luminance of some or all of lasers 1010R, 1010G, and 1010B, based on the age of a viewer of a virtual image, which is input to the vision-related information input unit 802. In other words, the information display device 1 adjusts a current value of each of the lasers 1010R, 1010G, and 1010B to obtain adjusted luminance. Thus, a displayed image can be perceived more easily by viewers, regardless of individual difference of visual faculties of a viewer. More specifically, as luminance of colors that are difficult for aged people to recognize are adjusted to be higher, visual faculties of aged people to see a virtual image are enhanced. The following description further explains the above effect, with reference to FIG. 7.

FIG. 7 is a drawing illustrating an example of a result of a subjectively-viewed evaluation whether luminance is high enough for a viewer to clearly perceive an image. The evaluation was performed on viewers viewing an image in blue color displayed by the information display device 1 with a blue-painted surface of a car on the background. Specifically, FIG. 7 is a drawing illustrating an example of a result of an evaluation performed on test-subjects regarding the following evaluation items: whether image content can be perceived; and whether brightness is not too high. The result indicates how bright an image is, compared to appropriate luminance, depending on age of a test-subject. Note that a dotted-pattern region in FIG. 7 indicates a range of comfortable luminance.

(1) of FIG. 7 is an example indicative of a conventional information display device, which is configured to display images in the same luminance regardless of age. In the configuration of (1), although test-subjects under the age of 60 found that the luminance was comfortable, as the age of a test-subject increased, perception of the blue image become increasingly difficult, with the result of dropping out of the region of comfortable luminance.

(2) of FIG. 7 is an example indicative of a conventional information display device, which is configured to display images in the same luminance regardless of age, but in higher luminance than (1). In the configuration of (2), although test-subjects over the age of 60 found the brightness to be comfortable, for test-subjects under the age of 60, brightness was too high and was out of the region of comfortable luminance.

(3) of FIG. 7 is an example indicative of the information display device 1 according to the first embodiment. In the configuration of (3), luminance of blue and green are increased for viewers over the age of 60, as illustrated in FIG. 6, based on the age of a viewer that is input to the vision-related information input unit 802. As a result, it is found that a displayed image (i.e. a virtual image) is comfortably perceivable for test-subjects of any age, because the information display device 1 enables an image to be perceivable for test-subjects at the age of 60 or more, and at the same time, enables the image not to be too bright for test-subjects aged under 60.

Note that the above description explains the case where an "age of a viewer" is input to the vision-related information input unit 802 as information relating to a viewer's vision of a virtual image. However, information relating to a viewer's vision of a virtual image, which is input to the vision-related information input unit 802, may be any information that has an influence on a viewer's visual faculties, and need not be restricted to age. For example, information relating to viewer's vision of a virtual image may be a "fatigue condition of a viewer", an "eyesight of a viewer", etc.

Furthermore, considering individual preferences, in addition to visual faculties, the information display device 1 may have a function of a viewer directly adjusting luminance values.

Modification of the First Embodiment

In the modification of the first embodiment, an example of adjusting a blue image into a red-tinged or green-tinged image is described.

For example, at Step S302 of FIG. 5, in a case where the age of a viewer is higher than a predetermined age (e.g. at the age of 60 or more), a default setting value of luminance of a light source of blue light, among multiple light sources, is added to a default setting value of luminance of either a light source of red light or a light source of green light, so as to adjust luminance of either the light source of red light or the light source of green light to be higher than the default setting value.

Specifically, for example, at Step S302 of FIG. 5, for a case where the age of a viewer is equal to or higher than 60, luminances are adjusted to be: IR2=IR1+IB1; IG2=IG1; and IB2=IB1, respectively. Alternatively, for a case where the age of a viewer is equal to or higher than 60, luminances are adjusted to be: IR2=IR1; IG2=IG1+IB1; and IB2=IB1, respectively.

Therefore, with respect to an image displayed with a light source of blue light, in the case where the age of a viewer is equal to or higher than 60, luminance of the light source of red light or the light source of green light is increased, so as to adjust the blue image into a red-tinged or green-tinged image. Thus, visibility of a virtual image is enhanced for aged people, who especially have difficulty seeing blue color.

Note that, in the above example, luminance of B (i.e. blue) may be additionally adjusted to be lower than the default setting value. In other words, in a case where the age of a viewer is equal to or higher than 60, luminance may be adjusted to be: IR2=IR1+IB1; IG2=IG1; IB2=α×IB1 (α<1), respectively. Alternatively, the luminance may be adjusted to be: IR2=IR1; IG2=IG1+IB1; and IB2=α×IB1 (α<1), respectively.

Second Embodiment

The following description regarding the second embodiment explains a case where an "existence of color weakness (i.e. whether a viewer has a color vision deficiency)" is input to the vision-related information input unit 802 as information relating to a viewer's vision of a virtual image. Note that existence of color weakness is information relating to a viewer's vision of a virtual image because visibility of each color of RGB changes, depending on existence of color weakness.

In a case where a viewer has a color vision deficiency, the luminance adjusting unit can adjust, for example, luminance of the light source of red light and the light source of green light, among multiple light sources, to be higher than in a case where a viewer does not have a color vision deficiency. More specific explanation is as follows.

FIG. 8 is a flowchart illustrating an example of luminance adjustment according to the second embodiment. First, at Step S401, existence of color weakness of a viewer of a virtual image is input through an input device such as a touchscreen or a keyboard, which is configured to be able to input information to the vision-related information input unit 802.

Information about existence of color weakness of a viewer of a virtual image that is input to the vision-related information input unit 802 is sent to the image data generating unit 820. Note that existence of color weakness of a viewer of a virtual image may be input through the input device by the viewer him/herself and may be input through the input device by a fellow passenger on a vehicle, etc., instead of the viewer.

Then, at Step S402, the luminance adjusting unit 8210 of the image data generating unit 820 performs luminance adjustment, based on existence of color weakness of a viewer that is received from the vision-related information input unit 802. For example, in a case where default setting values of the lasers 1010R, 1010G, and 1010B provided in the information display device 1 are luminance IR1, IG1, and IB1, respectively, the luminance adjusting unit 8210 adjusts the luminance IR1, IG1, and IB1 into luminance IR2, IG2, and IB2, respectively, based on existence of color weakness of a viewer that is received by the vision-related information input unit 802.

For example, the luminance IR2, IG2 and IB2 may be calculated by multiplying adjustment coefficients to the default setting values IR1, IG1 and IB1, respectively, based on existence of color weakness of a viewer that is received from the vision-related information input unit 802. For example, in a case where a viewer does not have color weakness, luminances are: IR2=IR1; IG2=IG1; and IB2=IB1, respectively; and in a case where a viewer has color weakness, luminances are adjusted to be: IR2=2.0×IR1; IG2=2.0×IG1; and IB2=IB1, respectively.

For example, in order to adjust luminance, relations between luminance IR1, IG1, and IB1 and luminance IR2, IG2, and IB2, respectively, depending on existence of color weakness may be stored in the ROM 203 in a table format or as coefficient data, so that the luminance adjusting unit 8210 can retrieve, from the ROM 203, an adjustment coefficient of luminance corresponding to existence of color weakness. An adjusted value of luminance is sent to the image rendering unit 840 as a part of image data.

Then, at Step S403, the control unit 8410 of the image rendering unit 840 controls the optical unit 10, based on image data, so as to irradiate the front windshield 910 with light. Here, a current value of each of the lasers 1010R, 1010G, and 1010B is independently controlled, based on the luminance value adjusted by the luminance adjusting unit 8210, so that a virtual image in desired luminance can be displayed.

As described above, in the second embodiment, the information display device 1 adjusts luminance (i.e. adjusts current values) of some or all of the lasers 1010R, 1010G, and 1010B, based on existence of color weakness of a viewer of a virtual image, which is input to the vision-related information input unit 802. Thus, as luminance of color that is difficult for people with color weakness to recognize is adjusted to be higher, visual faculties of people with color weakness to see a virtual image are enhanced.

Color weakness includes P-type (i.e. insensitive to red) and D-type (i.e. insensitive to green). By setting luminance of R and G to be higher (e.g. twice as high as default setting values) with respect to people with P-type and D-type color weakness, which are the most common (5% of Japanese male population) types, luminances of the light sources of red light and green light, which are difficult to sense, is adjusted to be higher than the default setting values, so as to be more perceivable. Thus, drivers with color weakness can comfortably perceive a displayed image (i.e. a virtual image) as well.

Third Embodiment

The following description regarding the third embodiment explains a case where a "test result of viewer's visual faculties" is input to the vision-related information input unit 802 as information relating to viewer's vision of a virtual image. Note that a test result of a viewer's visual faculties is a test result of visibility of each color of RGB, and therefore is information relating to a viewer's vision of a virtual image.

FIG. 9 is a flowchart illustrating an example of luminance adjustment according to the third embodiment. First, at Step S501, a test result of viewer's visual faculties is input through an input device such as a touchscreen or a keyboard, which is configured to be able to input information to the vision-related information input unit 802.

As illustrated in FIGS. 10A through 10C, an exemplary design for a test of visual faculties of a viewer is for a viewer to select an image that the viewer can perceive the most clearly among multiple images having different luminances for a testing purpose, which are virtual images projected on a front windshield and include surrounding images S and central images I1 through I3, respectively. The multiple images for a testing purpose having different luminances may be generated by means of the image data generating unit 820.

In FIGS. 10A through 10C, the surrounding images S and the images I1 through I3 are in the same color but luminance of the images I1 through I3 are higher. Furthermore, luminance of the image $I_1$ is higher than luminance of the image $I_2$, and luminance of the image $I_2$ is higher than luminance of the image $I_3$. Thus, it is possible to check, in a simulated manner, suitable luminance for a viewer's visibility of a virtual image in relation to a background image. Then, in a case where an image with higher luminance is selected among the images I1 through I3, the adjustment coefficient is determined to be greater, proportionally.

For example, by use of following formulas: IR2=R(TEST)×IR1; IG2=G(TEST)×IG1; and IB2=B(TEST)×B1; in a case where the image $I_1$ is selected, R(TEST), G(TEST), and B(TEST), which are adjustment coefficients of luminance, are determined to be 1, respectively. Furthermore, in a case where the image $I_2$ is selected, R(TEST), G(TEST), and B(TEST) are determined to be 2, respectively. Furthermore, in a case where the image $I_3$ is selected, R(TEST), G(TEST), and B(TEST) are determined to be 3, respectively.

As adjustment coefficients of luminance are determined, based on a test result, as described above, luminance can be adjusted to be suitable for visual faculties and preference of a viewer, compared to a simple adjustment such as simply increasing luminance in a case of an aged person.

Additionally, the test is not limited to the example of FIGS. 10A through 10C; for example, the test may be performed against an actual background while driving, instead of a simulated background (i.e. the surrounding image S in FIGS. 10A through 10C).

Although preferred embodiments of the present invention are explained above, the present invention is not limited to the embodiments, and variations and replacements of the above embodiments may be made without departing from the scope of the present invention.

For example, although an example of an information display device including laser light sources is provided in the above embodiments, the present invention is applicable to an information display device including light emitting diodes (LEDs) instead of laser light sources. However, as laser light sources can produce colors that are further different from background colors (i.e. colors other than natural absorption colors), it is preferable to employ laser light sources, compared to employing LEDs, so as to display images that viewers can easily perceive. That is to say, RGB light sources of LEDs have broad wavelength ranges, and therefore only achieve a color-reproduction range that is wide enough to reproduce natural absorption colors (c.f. JapanColor). However, RGB light sources of laser light sources have narrower wavelength ranges, and therefore achieve a color-reproduction range that is wide enough to reproduce wider ranges of colors in addition to natural absorption colors (c.f. JapanColor).

Furthermore, although, in the above embodiment, the above description explains a case where an information display device according to the present invention is an HuD, the information display device according to the present invention is not limited to an HuD; the present invention is applicable to any device that superimposes a virtual image, etc., of a light source image onto a background. For example, the information display device may be a head mount display (HMD), etc.

The present application is based on Japanese priority application No. 2016-102552 filed on May 23, 2016, with the Japanese Patent Office, the entire content of which is hereby incorporated by reference.

REFERENCE SIGNS LIST 1 information display device
10 optical unit
20 electronics unit
101 light source unit
102 light deflector
103 mirror
104 screen
105 concave mirror
201 FPGA
202 CPU
203 ROM
204 RAM
205 I/F
206 bus-line
207 LD driver
208 MEMS controller
800 vehicle-information input unit
801 external information input unit
802 vision-related information input unit
820 image data generating unit
840 image rendering unit
1010R, 1010G, 1010B lasers
1011 light-path integrating unit
1012 optical system
8210 luminance adjusting unit
8410 control unit

The invention claimed is:

1. An information display device for irradiating a transparent-reflective member with light for forming an image, in order to display a virtual image of the image on the transparent-reflective member, the information display device comprising:
a plurality of light sources having different peak emission wavelengths, respectively, which are provided for generating the light for forming the image;
vision-related information input circuitry configured to receive an input of information relating to vision of a viewer viewing the virtual image; and
luminance adjusting circuitry configured to adjust luminance of each of the plurality of light sources, independently, based on the information input into the vision-related information input circuitry,
wherein the information is whether the viewer has a color vision deficiency.

2. The information display device according to claim 1, wherein the information is an age of the viewer.

3. An information display device for irradiating a transparent-reflective member with light for forming an image, in order to display a virtual image of the image on the transparent-reflective member, the information display device comprising:
a plurality of light sources having different peak emission wavelengths, respectively, which are provided for generating the light for forming the image;
vision-related information input circuitry configured to receive an input of information relating to vision of a viewer viewing the virtual image; and
luminance adjusting circuitry configured to adjust luminance of each of the plurality of light sources, independently, based on the information input into the vision-related information input circuitry,
wherein the information is an age of the viewer, and
wherein the luminance adjusting circuitry adjusts luminance of one of the plurality of light sources to be higher than a default setting value of luminance of the one of the plurality of light sources, the one of the plurality of light sources having a peak emission wavelength of less than 520 nm, and
wherein luminance of the one of the plurality of light sources is adjusted, such that luminance of the one of the plurality of light sources increases as the age of the viewer increases.

4. An information display device for irradiating a transparent-reflective member with light for forming an image, in order to display a virtual image of the image on the transparent-reflective member, the information display device comprising:
a plurality of light sources having different peak emission wavelengths, respectively, which are provided for generating the light for forming the image;
vision-related information input circuitry configured to receive an input of information relating to vision of a viewer viewing the virtual image; and
luminance adjusting circuitry configured to adjust luminance of each of the plurality of light sources, independently, based on the information input into the vision-related information input circuitry,
wherein the information is an age of the viewer, and
wherein, in a case where the age of the viewer is equal to or higher than a predetermined age, the luminance adjusting circuitry adjusts luminance of one of the plurality of light sources to be higher than in a case where the age of the viewer is lower than the predetermined age, the one of the plurality of light sources having a peak emission wavelength of less than 520 nm.

5. The information display device according to claim 3, wherein the one of the plurality of light sources having the peak emission wavelength of less than 520 nm is a light source for generating blue light.

6. The information display device according to claim 2, wherein the plurality of light sources include a light source for generating blue light, a light source for generating red light, and a light source for generating green light,
wherein, in a case where the age of the viewer is equal to or more than a predetermined age, the luminance adjusting circuitry adds a default setting value of luminance of the light source for generating blue light to a default setting value of luminance of the light source for generating red light or the light source for generating green light, so as to adjust luminance of the light source for generating red light or the light source for generating green light to be higher than the default setting value of luminance of the light source for generating red light or the light source for generating green light.

7. The information display device according to claim 6, wherein, in the case where the age of the viewer is equal to or more than a predetermined age, the luminance adjusting circuitry adjusts luminance of the light source for generating blue light to be lower than the default setting value of luminance of the light source for generating blue light.

8. The information display device according to claim 1, wherein, in a case where the viewer has a color vision deficiency, the luminance adjusting circuitry adjusts luminance of a light source for generating red light and a light source for generating green light to be higher than default setting values of luminance of the light source for generating red light and the light source for generating green light, respectively, the light source for generating red light and the light source for generating green light being included in the plurality of light sources.

9. The information display device according to claim 1, wherein, in a case where the viewer has a color vision deficiency, the luminance adjusting circuitry adjusts luminance of a light source for generating red light and a light source for generating green light to be higher than in a case where the viewer does not have a color vision deficiency, the light source for generating red light and the light source for generating green light being included in the plurality of light sources.

10. The information display device according to claim 1 further comprising:
   image data generating circuitry configured to generate data representing a plurality of images for a testing purpose, the plurality of images for a testing purpose having different luminances, respectively; and
   image rendering circuitry configured to display a virtual image of the plurality of images for a testing purpose, and
   wherein the information is an indication of one of the plurality of images for a testing purpose, the one of the plurality of images for a testing purpose being selected by a viewer viewing the virtual image of the plurality of images for a testing purpose.

11. The information display device according to claim 1, wherein the plurality of light sources are laser light sources.

* * * * *